United States Patent [19]
Codina et al.

[11] Patent Number: 5,631,568
[45] Date of Patent: May 20, 1997

[54] CAPACITIVE OIL LIFE SENSOR

[75] Inventors: George Codina, North Hollywood, Calif.; Donna J. Murr, Dunlap; Chandrasekar Ramamoorthy, Normal, both of Ill.

[73] Assignee: Caterpillar Inc., Peoria, Ill.

[21] Appl. No.: 522,472

[22] Filed: Aug. 31, 1995

[51] Int. Cl.$^6$ .................................................. G01R 27/26
[52] U.S. Cl. ........................ 324/690; 73/61.44; 324/663
[58] Field of Search ............................... 324/678, 663; 73/861.08, 61.44; 340/603

[56] References Cited

U.S. PATENT DOCUMENTS

| | | | |
|---|---|---|---|
| 3,595,078 | 7/1971 | Beck et al. | 73/194 |
| 3,635,082 | 1/1972 | Prellwitz et al. | 73/194 |
| 3,802,261 | 4/1974 | Zimmerman et al. | 73/194 |
| 4,074,184 | 2/1978 | Dechene et al. | 324/30 |
| 4,240,028 | 12/1980 | Davis, Jr. | 324/61 |
| 4,266,188 | 5/1981 | Thompson | 324/65 |
| 4,468,611 | 8/1984 | Tward | 324/61 |
| 4,604,904 | 8/1986 | Massen | 73/861 |
| 4,658,208 | 4/1987 | Lee et al. | 324/61 |
| 4,713,603 | 12/1987 | Thorn | 324/61 |
| 4,714,048 | 12/1987 | Jefferies et al. | 119/14.08 |
| 4,751,842 | 6/1988 | Ekrann et al. | 73/61.1 |
| 4,894,604 | 1/1990 | Dowling et al. | 324/690 |
| 4,920,795 | 5/1990 | Codazzi et al. | 73/195 |
| 5,274,335 | 12/1993 | Wang et al. | 324/663 |
| 5,367,264 | 11/1994 | Brabetz | 324/663 |
| 5,382,942 | 1/1995 | Raffa et al. | 340/457 |
| 5,503,004 | 4/1996 | Agar | 73/61.44 |

OTHER PUBLICATIONS

SAE Technical Paper Series—910497 Feb. 25–Mar. 1, 1991 "A Capacitive Oil Deterioration Sensor".

*Primary Examiner*—Maura K. Regan
*Attorney, Agent, or Firm*—James R. Yee

[57] ABSTRACT

An apparatus for determining the remaining life of hydraulic fluid in a hydraulic system having a hydraulic container includes a capacitor formed by a pair of electrodes. A charging circuit produces a charging current of constant magnitude. The charging current is used to charge the capacitor to a predetermined voltage. A timing circuit measures the elapsed time between the time at which the charging circuit begins to produce the charging current and the time at which the capacitor has been charged to the predetermined voltage. The timing circuit also produces a pulse width modulated signal. The magnitude of the pulse width modulated signal is indicative of the time difference. A controller receives the pulse width modulated signal and determines the life of the hydraulic fluid.

4 Claims, 2 Drawing Sheets

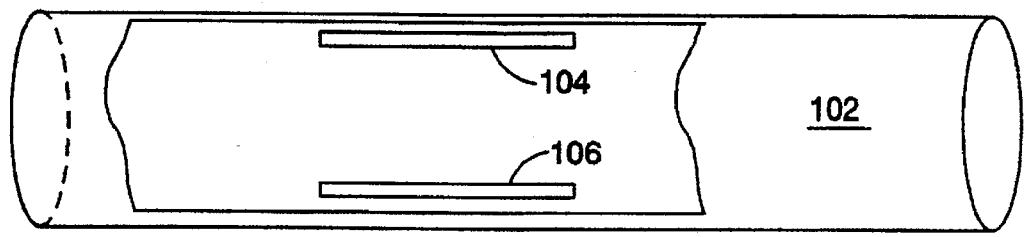
Fig_1_
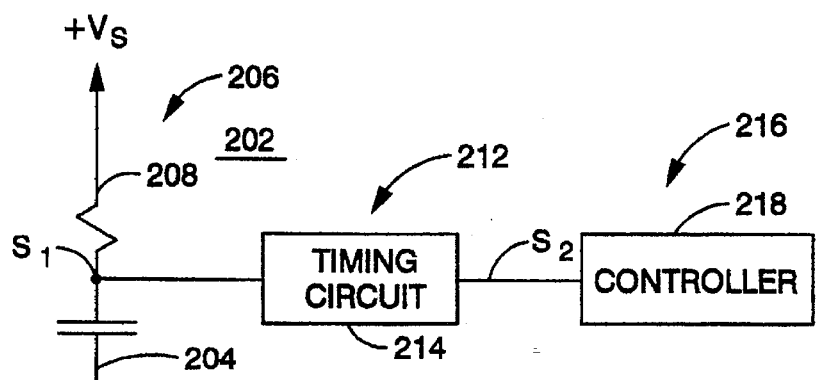
Fig_2_
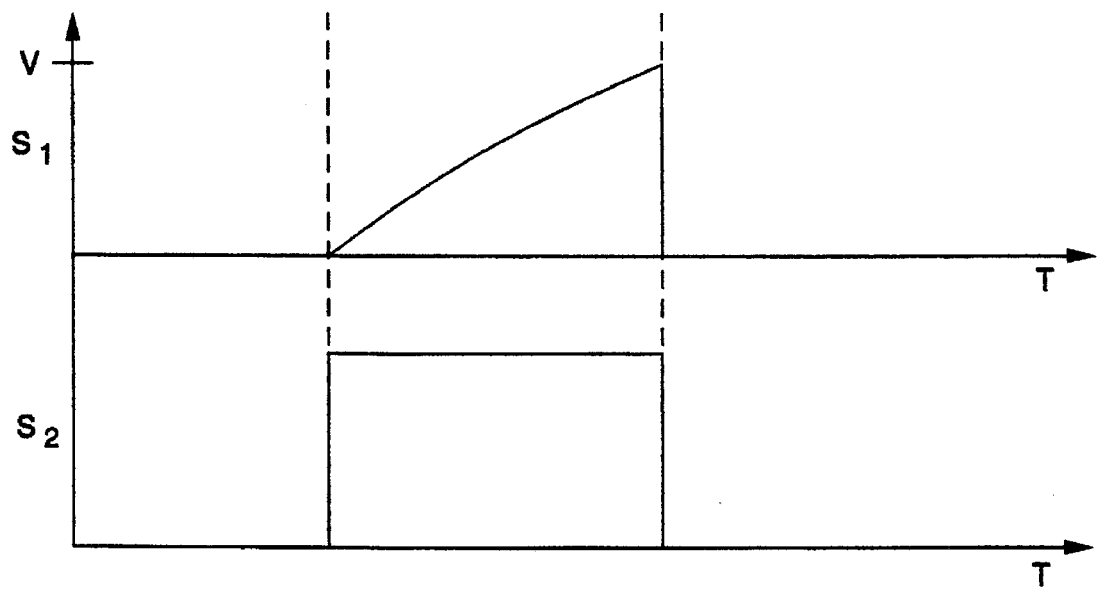
Fig_3_

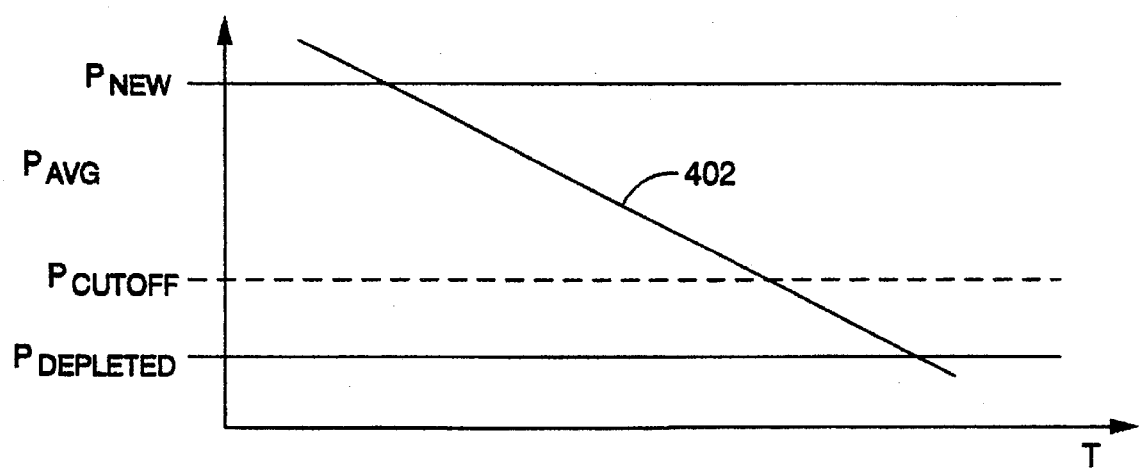
Fig_4_
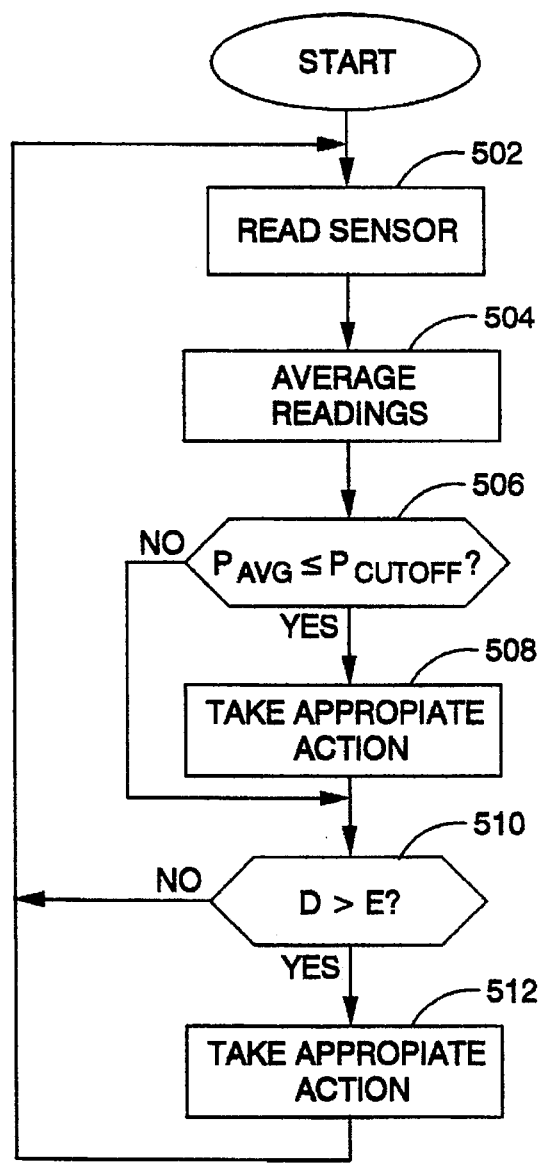
Fig_5_

CAPACITIVE OIL LIFE SENSOR

TECHNICAL FIELD

This invention relates generally to hydraulic systems, and more particularly, to a capacitive sensor which determines the life of hydraulic fluid within a hydraulic system.

1. Background Art

In the earthmoving industry, hydraulic systems are typically used to power earthmoving machines and/or their implements. Earthmoving machines operate in a highly hostile environment. One of the many problems that occur in hydraulic systems is oil breakdown. Oil breakdown occurs through the normal operation of the system. Typically the oil is changed according to a scheduled time table. However, variations in the operation of the machine may speed up breakdown of the oil before the next scheduled oil change.

The present invention is directed to overcoming one or more of the problems, as set forth above.

2. Disclosure of the Invention

An apparatus for determining the life of hydraulic fluid in a hydraulic system having a hydraulic container is provided. The apparatus includes a capacitor formed by a pair of electrodes. A charging circuit produces a charging current of constant magnitude. The charging current is used to charge the capacitor to a predetermined voltage. A timing circuit measures the elapsed time between the time at which the charging circuit begins to produce the charging current and the time at which the capacitor has been charged to the predetermined voltage. The timing circuit also produces a pulse width modulated signal. The magnitude of the pulse width modulated signal is indicative of the time difference. A controller receives the pulse width modulated signal and determines the life of the hydraulic fluid.

BRIEF DESCRIPTION OF THE DRAWINGS

FIG. 1 is a diagrammatic view of a container for containing fluid;

FIG. 2 is a block diagram of an oil life sensor according to an embodiment of the present invention;

FIG. 3 is a graphical illustration of relevant signals within the oil life sensor of FIG. 1;

FIG. 4 is a graphical illustration of another relevant signal within the oil life sensor of FIG. 1; and, FIG. 5 is a flow diagram illustrating operation of the oil life sensor of FIG. 2.

BEST MODE FOR CARRYING OUT THE INVENTION

With reference to FIG. 1, the present invention is adapted to determine or predict the life of oil in a hydraulic system.

With reference to FIGS. 1 and 2, the present invention, apparatus or detector 202 includes a pair of electrodes contained within a container 102. The electrodes 104, 106 are contained within the container 102 and are oppositely spaced so as to form a capacitor 204. The hydraulic fluid within the container 102 is the dielectric of the capacitor 204. The electrodes may be flat or curved and/or rectangular, triangular, or otherwise shaped. The container 102 refers to any receptacle for containing fluid, or a tube, pipe or similar device for transporting fluid.

A charging means 206 is connected to the capacitor 204. In the preferred embodiment, the charging means 206 includes a resistor 208 and a source of constant voltage, $V_s$.

The charging means 206 produces a charging current of constant magnitude. The charging current charges the capacitor 204 until a predetermined voltage (V) across the capacitor is reached. The magnitude of the charging current is determined by the resistance value of the resistor.

Preferably, the resistor is variable to allow for adjustment of the sensor 202. For example, an exemplar charging current, resistance value and predetermined voltage for determining oil life are 90 microamps, 100 KOhms, and 9 volts respectively. The charging current will vary from system to system and will be determined to minimize or eliminate the effects of other system parameters, e.g., fluid flow, pressure, cavitation, on the charging time.

The effects of fluid temperature variations is preferably minimized by heating the electrodes 104, 106.

A timing means 212 is also connected to the capacitor 204. The timing means 212 includes a timing circuit 214. The timing circuit 214 detects the time at which the charging circuit begins to produce the charging current and the time at which the capacitor has been charged to the predetermined voltage. The timing circuit also produces a pulse width modulated signal. The magnitude of the pulse width modulated signal is indicative of the elapsed time between the time at which the charging circuit begins to produce the charging current and the time at which the capacitor has been charged to the predetermined voltage. In the preferred embodiment, the magnitude of the pulse width modulated signal is equal to the duration of each pulse.

In the preferred embodiment, the timing means 212 includes a MC1555 timing integrated circuit which is available from Motorola Corp., of Schaumburg Ill. The MC1555 circuit advantageously senses when the capacitor 204 has reached the predetermined voltage and responsively discharges the capacitor into electrical ground.

With reference to FIG. 3, $S_1$ represents the voltage across the capacitor and $S_2$ represents the output of the timing circuit 214.

A controlling means 216 receives the pulse width modulated signal from the timing means 212 and determines the life of the hydraulic fluid in the container 102. The controlling means 216 includes a controller 218 which preferably is microprocessor controlled.

Oil breakdown will cause a decrease in the pulse width over time. By averaging the pulse width over time and comparing the average pulse with the reference pulse widths for new oil and completely depleted or substantially depleted oil, the oil life can be determined. Oil life may be defined as the time at which an oil change is required.

As shown in FIG. 4, the averaged pulse widths ($P_{avg}$) from the sensor are compared with pulse width references for new oil ($P_{NEW}$) and for depleted oil ($P_{DEPLETED}$) $P_{NEW}$ and $P_{DEPLETED}$ are predetermined experimentally. The container 102 represents the expected breakdown of the oil. It should be noted that actual breakdown as represented by pulse width may not be linear. A cutoff value for the pulse width ($PC_{CUTOFF}$) is also predetermined. Once $P_{AVG}$ reaches $P_{CUTOFF}$, an oil change is required. Thus, the controller 218 monitors $P_{AVG}$ and takes appropriate action when $P_{AVG}$ reaches $P_{CUTOFF}$.

Additionally, the controlling means 216 includes means which detects abnormal changes in the hydraulic oil, i.e., unexpected changes in the deterioration of the hydraulic oil. This is accomplished by comparing the rate of change (D) in the width of the pulses of the pulse width modulated signal with a predetermined set value (E). If the rate of change exceeds the predetermined set value (D>E), then the controlling means produces an error signal. The error signal may consist of logging the event in a memory and/or a signal to the operator via an indicator lamp.

With respect to FIG. 5, the operation of the controlling means 216 will now be discussed. In a first control block 502, the sensor is read. In a second control block 504, the sensor reading is averaged with past sensor readings. If, in a first decision block 506, the average is less than or equal to $P_{CUTOFF}$, then control proceeds to a third control block 508. Otherwise, control proceeds to a second decision block 510.

In the third control block 508, the appropriate action is taken, i.e., signaling a CHANGE OIL CONDITION. Appropriate action may include activating an indicator lamp and/or recording the event in a memory.

In the second decision block 510, if D>E, then control proceeds to a fourth control block 512. Otherwise control returns to the first control bock 502. In the fourth control block 512, the controlling means 216 takes the appropriate action.

INDUSTRIAL APPLICABILITY

With reference to FIGS. 1 and 2, the present invention is adapted to detect the life of oil in a hydraulic system.

With reference to FIG. 3, the operation of the sensor 202 is discussed below. The charging circuit 210 produces a charging current. The charging current has a constant magnitude. The charging circuit 210 via the charging current charges the capacitor 204 until it reaches a predetermined voltage, at which time the charging current is stopped and the energy stored in the capacitor is allowed to dissipate. $S_1$ refers to the voltage across the capacitor 204.

The timing circuit 214 detects the time at which the charging circuit 210 begins to supply the charging current and detects the time at which the capacitor 204 has reached the predetermined voltage level. The timing circuit 214 produces a pulse width modulated signal ($S_2$). Each pulse has a duration equal to the difference between the time at which the charging circuit 210 begins to supply the charging current and the time at which the capacitor 204 has reached the predetermined voltage level.

The controlling means 216 receives the pulse width modulated signal from the timing means 212 and determines the life of the hydraulic fluid. Oil breakdown will cause a decrease in the output pulse width over time. By averaging the pulse width over time and comparing the average pulse width to the reference pulse widths of new oil and completely deplete oil, the useful oil life can be determined as the time at which an oil change is required.

Other aspects, objects, and features of the present invention can be obtained from a study of the drawings, the disclosure, and the appended claims.

We claim:

1. An apparatus for determining the life of hydraulic fluid in a hydraulic system having a hydraulic container, comprising:

a pair of electrodes contained within the container and being oppositely spaced, forming a capacitor;

charging means, coupled to said capacitor, for producing a charging current of constant magnitude and charging said capacitor to a predetermined voltage;

timing means, connected to said capacitor, for detecting the time at which said charging means begins to produce said charging current and the time at which said capacitor has been charged to said predetermined voltage, and for producing a pulse width modulated signal, the magnitude of said pulse width modulated signal being indicative of a charging time, said charging time defined as the time between the start of said constant current and the time at which said capacitor has been charged to said predetermined voltage and being indicative of the life of the hydraulic fluid, a magnitude of said charging current chosen to minimize the effects of other parameters on said charging time; and, controlling means for receiving said pulse width modulated signal and responsively determining the life of the hydraulic fluid.

2. An apparatus, as set forth in claim 1, wherein said controlling means includes means for determining an average width of consecutive pulses of said pulse width modulated signal.

3. An apparatus, as set forth in claim 2, wherein said controlling means includes means for comparing said average width to a predetermined cutoff value and responsively signaling a CHANGE OIL CONDITION.

4. An apparatus, as set forth in claim 1, wherein said controlling means includes means for determining the rate of change in the width of the pulses of said pulse width modulated signal, comparing said rate of change with a predetermined value and producing an error signal in response to said rate of change exceeding said predetermined value.

* * * * *